(12) United States Patent
Blasco et al.

(10) Patent No.: US 9,487,519 B2
(45) Date of Patent: Nov. 8, 2016

(54) 5,6-DIALKYL-7-AMINOTRIAZOLOPYRIMIDINES, THEIR PREPARATION AND THEIR USE FOR CONTROLLING HARMFUL FUNGI, AND COMPOSITIONS COMPRISING THESE COMPOUNDS

(75) Inventors: Jordi Tormo i Blasco, Laudenbach (DE); Carsten Blettner, Mannheim (DE); Bernd Müller, Frankenthal (DE); Markus Gewehr, Kastellaun (DE); Wassilios Grammenos, Ludwigshafen (DE); Thomas Grote, Wachenheim (DE); Joachim Rheinheimer, Ludwigshafen (DE); Peter Schäfer, Ottersheim (DE); Frank Schieweck, Heβheim (DE); Anja Schwögler, Mannheim (DE); Oliver Wagner, Neustadt (DE); Matthias Niedenbrück, Limburgerhof (DE); Maria Scherer, Godramstein (DE); Siegfried Strathmann, Limburgerhof (DE); Ulrich Schöfl, Brühl (DE); Reinhard Stierl, Freinsheim (DE)

(73) Assignee: BASF SE, Ludwigshafen (DE)

( * ) Notice: Subject to any disclaimer, the term of this patent is extended or adjusted under 35 U.S.C. 154(b) by 1356 days.

(21) Appl. No.: 10/589,953

(22) PCT Filed: Mar. 8, 2005

(86) PCT No.: PCT/EP2005/002427
§ 371 (c)(1),
(2), (4) Date: Aug. 18, 2006

(87) PCT Pub. No.: WO2005/087773
PCT Pub. Date: Sep. 22, 2005

(65) Prior Publication Data
US 2007/0173408 A1  Jul. 26, 2007

(30) Foreign Application Priority Data

Mar. 10, 2004  (DE) ........................ 10 2004 012 011

(51) Int. Cl.
C07D 487/04    (2006.01)
(52) U.S. Cl.
CPC .................................. C07D 487/04 (2013.01)
(58) Field of Classification Search
CPC .................................................... C07D 487/04
USPC ................ 514/383, 257, 259.1; 504/100
See application file for complete search history.

(56) References Cited

U.S. PATENT DOCUMENTS

| | | | | | |
|---|---|---|---|---|---|
| 4,617,303 | A | * | 10/1986 | Eicken et al. | 514/259.3 |
| RE32,676 | E | * | 5/1988 | Eicken et al. | 514/259.3 |
| 5,756,509 | A | * | 5/1998 | Pees | 514/259.31 |
| 5,854,252 | A | * | 12/1998 | Pees et al. | 514/259.31 |
| 7,307,172 | B2 | * | 12/2007 | Blasco et al. | 548/262.4 |
| 7,501,383 | B2 | * | 3/2009 | Tormo I Blasco et al. | 504/100 |

FOREIGN PATENT DOCUMENTS

| | | |
|---|---|---|
| CA | 1 288 096 | 8/1991 |
| CA | 1288096 | 8/1991 |
| CA | 2 454 542 | 2/2003 |
| CA | 2 454 542 A1 | 2/2003 |
| EP | 0141317 A2 | 10/1984 |
| EP | 0 141 317 | 5/1985 |
| EP | 0 215 382 | 3/1987 |
| EP | 0215382 A1 | 3/1987 |
| EP | 0 614 113 | 9/1994 |
| EP | 0 614 113 A2 | 9/1994 |
| EP | 0 770 615 | 5/1997 |
| EP | 0 0770 615 A1 | 5/1997 |
| GB | 1 148 629 | 4/1969 |
| GB | 1 148 629 A | 4/1969 |
| WO | WO 03/009687 | 2/2003 |
| WO | WO-03/009687 A1 | 2/2003 |

OTHER PUBLICATIONS

International Search Report for International Application No. PCT/EP2005/002427.
International Preliminary Report on Patentability for International Application No. PCT/EP2005/002427.

* cited by examiner
(Continued)

*Primary Examiner* — Sabiha N Qazi
(74) *Attorney, Agent, or Firm* — Brinks Gilson & Lione

(57) ABSTRACT

5,6-Dialkyl-7-aminotriazolopyrimidines of the formula I

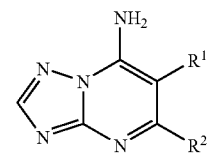

in which the substituents are as defined below:
$R^1$ is alkyl or alkoxyalkyl, where the aliphatic groups may be substituted as defined in the description;
$R^2$ is $CHR^3CH_3$, cyclopropyl, $CH=CH_2$ or $CH_2CH=CH_2$;
$R^3$ is hydrogen, $CH_3$ or $CH_2CH_3$;
processes for preparing these compounds, compositions comprising them and their use for controlling phytopathogenic harmful fungi.

10 Claims, No Drawings

5,6-DIALKYL-7-AMINOTRIAZOLOPYRIMIDINES, THEIR PREPARATION AND THEIR USE FOR CONTROLLING HARMFUL FUNGI, AND COMPOSITIONS COMPRISING THESE COMPOUNDS

The present invention relates to 5,6-dialkyl-7-aminotriazolopyrimidines of the formula I

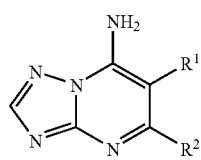

in which the substituents are as defined below:
$R^1$ is $C_5$-$C_{12}$-alkyl or $C_5$-$C_{14}$-alkoxyalkyl, where the aliphatic groups may be substituted by 1 to 3 of the following groups:
  cyano, nitro, hydroxyl, $C_3$-$C_6$-cycloalkyl, $C_1$-$C_6$-alkylthio and $NR^aR^b$;
$R^a$, $R^b$ are hydrogen or $C_1$-$C_6$-alkyl;
$R^2$ is $CHR^3CH_3$, cyclopropyl, $CH{=}CH_2$ or $CH_2CH{=}CH_2$;
$R^3$ is hydrogen, $CH_3$ or $CH_2CH_3$.

Moreover, the invention relates to processes for preparing these compounds, to compositions comprising them and to their use for controlling phytopathogenic harmful fungi.

5,6-Dialkyl-7-aminotriazolopyrimidines are proposed in a general manner in GB 1 148 629. Individual fungicidally active 5,6-dialkyl-7-aminotriazolopyrimidines are known from EP-A 141 317. However, in many cases their activity is unsatisfactory. Based on this, it is an object of the present invention to provide compounds having improved activity and/or a widened activity spectrum.

We have found that this object is achieved by the compounds defined at the outset. Furthermore, we have found processes and intermediates for their preparation, compositions comprising them and methods for controlling harmful fungi using the compounds I.

The compounds of the formula I differ from those in the abovementioned publications by the specific arrangement of the substituent in the 5-position of the triazolopyrimidine skeleton.

Compared to the known compounds, the compounds of the formula I are more effective against harmful fungi.

The compounds according to the invention can be obtained by different routes. Advantageously, the compounds according to the invention are obtained by converting substituted β-keto esters of the formula II with 3-amino-1,2,4-triazole of the formula III to give 7-hydroxytriazolopyrimidines of the formula IV. The groups $R^1$ and $R^2$ in formulae II and IV are as defined for formula I and the group R in formula II is $C_1$-$C_4$-alkyl; for practical reasons, preference is given here to methyl, ethyl or propyl.

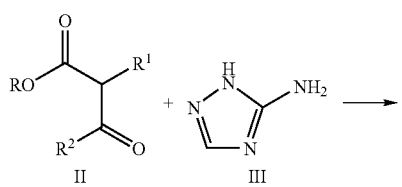

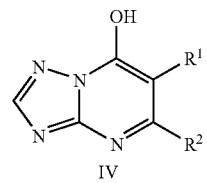

The reaction of the substituted β-keto esters of the formula II with the aminoazoles of the formula III can be carried out in the presence or absence of solvents. It is advantageous to use solvents to which the starting materials are substantially inert and in which they are completely or partially soluble. Suitable solvents are in particular alcohols, such as ethanol, propanols, butanols, glycols or glycol monoethers, diethylene glycols or their monoethers, aromatic hydrocarbons, such as toluene, benzene or mesitylene, amides, such as dimethylformamide, diethylformamide, dibutylformamide, N,N-dimethylacetamide, lower alkanoic acids, such as formic acid, acetic acid, propionic acid, or bases, such as alkali metal and alkaline earth metal hydroxides, alkali metal and alkaline earth metal oxides, alkali metal and alkaline earth metal hydrides, alkali metal amides, alkali metal and alkaline earth metal carbonates and also alkali metal bicarbonates, organometallic compounds, in particular alkali metal alkyls, alkylmagnesium halides and also alkali metal and alkaline earth metal alkoxides and dimethoxymagnesium, moreover organic bases, for example tertiary amines, such as trimethylamine, triethylamine, triisopropylamine, tributylamine and N-methylpiperidine, N-methylmorpholine, pyridine, substituted pyridines, such as collidine, lutidine and 4-dimethylaminopyridine, and also bicyclic amines and mixtures of these solvents with water. Suitable catalysts are bases, as mentioned previously, or acids, such as sulfonic acids or mineral acids. With particular preference, the reaction is carried out without solvent or in chlorobenzene, xylene, dimethyl sulfoxide or N-methylpyrrolidone. Particularly preferred bases are tertiary amines, such as triisopropylethylamine, tributylamine, N-methylmorpholine or N-methylpiperidine. The temperatures are from 50 to 300° C., preferably from 50 to 180° C., if the reaction is carried out in solution [cf. EP-A 770 615; Adv. Het. Chem. 57 (1993), 81ff].

The bases are generally employed in catalytic amounts; however, they can also be employed in equimolar amounts, in excess or, if appropriate, as solvent.

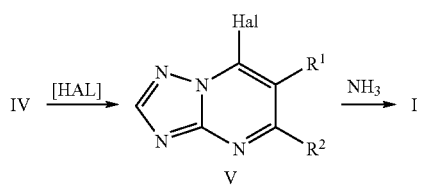

In most cases, the resulting condensates of the formula IV precipitate from the reaction solutions in pure form and, after washing with the same solvent or with water and subsequent drying, they are reacted with halogenating agents, in particular chlorinating or brominating agents, to give the compounds of the formula V in which Hal is chlorine or bromine, in particular chlorine. The reaction is preferably carried out using chlorinating agents such as phosphorus oxychloride, thionyl chloride or sulfonyl chloride at from 50° C. to 150° C., preferably in excess phosphorus oxytrichloride at reflux temperature. After evaporation of excess phosphorus oxytrichloride, the residue is treated with ice-water, if appropriate with addition of a water-immiscible solvent. In most cases, the chlorinated product isolated from the dried organic phase, if appropriate after evaporation of the inert solvent, is very pure and is subsequently reacted with ammonia in inert solvents at from 100° C. to 200° C. to give the 7-amino-triazolo[1,5-a]pyrimidines. This reaction is preferably carried out using a 1- to 10-molar excess of ammonia, under a pressure of from 1 to 100 bar.

The novel 7-aminoazolo[1,5-a]pyrimidines are, if appropriate after evaporation of the solvent, isolated as crystalline compounds, by digestion in water.

The β-keto esters of the formula II can be prepared as described in Organic Synthesis Coll. Vol. 1, p. 248, and/or they are commercially available.

Alternatively, the novel compounds of the formula I can be obtained by reacting substituted acyl cyanides of the formula VI in which $R^1$ and $R^2$ are as defined above with 3-amino-1,2,4-triazole of the formula III.

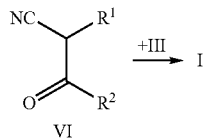

The reaction can be carried out in the presence or absence of solvents. It is advantageous to use solvents to which the starting materials are substantially inert and in which they are completely or partially soluble. Suitable solvents are in particular alcohols, such as ethanol, propanols, butanols, glycols or glycol monoethers, diethylene glycols or their monoethers, aromatic hydrocarbons, such as toluene, benzene or mesitylene, amides, such as dimethylformamide, diethylformamide, dibutylformamide, N,N-dimethylacetamide, lower alkanoic acids, such as formic acid, acetic acid, propionic acid, or bases, such as those mentioned above, and mixtures of these solvents with water. The reaction temperatures are from 50 to 300° C., preferably from 50 to 150° C., if the reaction is carried out in solution.

The novel 7-aminotriazolo[1,5-a]pyrimidines are, if appropriate after evaporation of the solvent or dilution with water, isolated as crystalline compounds.

Some of the substituted alkyl cyanides of the formula VI required for preparing the 7-aminoazolo[1,5-a]pyrimidines are known, or they can be prepared by known methods from alkyl cyanides and carboxylic esters using strong bases, for example alkali metal hydrides, alkali metal alkoxides, alkali metal amides or metal alkyls (cf.: J. Amer. Chem. Soc. 73, (1951), p. 3766).

If individual compounds I cannot be obtained by the routes described above, they can be prepared by derivatization of other compounds I.

If the synthesis yields mixtures of isomers, a separation is generally not necessarily required since in some cases the individual isomers can be interconverted during work-up for use or during application (for example under the action of light, acids or bases). Such conversions may also take place after use, for example, in the case of treatment of plants, in the treated plants, or in the harmful fungus to be controlled.

In the definitions of symbols given above, collective terms were used which are generally representative of the following substituents:

halogen: fluorine, chlorine, bromine and iodine;

alkyl: saturated straight-chain or mono- or dibranched hydrocarbon radicals having 1 to 4 or 5 to 12 carbon atoms, for example $C_1$-$C_6$-alkyl such as methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

halomethyl: a methyl group in which some or all of the hydrogen atoms may be replaced by halogen atoms as mentioned above; in particular chloromethyl, bromomethyl, dichloromethyl, trichloromethyl, fluoromethyl, difluoromethyl, trifluoromethyl, chlorofluoromethyl, dichlorofluoromethyl, chlorodifluoromethyl;

cycloalkyl: mono- or bicyclic saturated hydrocarbon groups having 3 to 6 carbon ring members, such as cyclopropyl, cyclobutyl, cyclopentyl and cyclohexyl;

alkoxyalkyl: a saturated straight-chain or mono-, di- or tribranched hydrocarbon chain which is interrupted by an oxygen atom, for example $C_5$-$C_{12}$-alkoxyalkyl: a hydrocarbon chain as described above having 5 to 12 carbon atoms which may be interrupted by an oxygen atom in any position, such as propoxyethyl, butoxyethyl, pentoxyethyl, hexyloxyethyl, heptyloxyethyl, octyloxyethyl, nonyloxyethyl, 3-(3-ethylhexyloxy)ethyl, 3-(2,4,4-trimethylpentyloxy)ethyl, 3-(1-ethyl-3-methylbutoxy)ethyl, ethoxypropyl, propoxypropyl, butoxypropyl, pentoxypropyl, hexyloxypropyl, heptyloxypropyl, octyloxypropyl, nonyloxypropyl, 3-(3-ethylhexyloxy)propyl, 3-(2,4,4-trimethylpentyloxy) propyl, 3-(1-ethyl-3-methylbutoxy)propyl, ethoxybutyl, propoxybutyl, butoxybutyl, pentoxybutyl, hexyloxybutyl, heptyloxybutyl, octyloxybutyl, nonyloxybutyl, 3-(3-ethylhexyloxy)butyl, 3-(2,4,4-trimethylpentyloxy)butyl, 3-(1-ethyl-3-methylbutoxy)butyl, methoxypentyl, ethoxypentyl, propoxypentyl, butoxypentyl, pentoxypentyl, hexyloxypentyl, heptyloxypentyl, 3-(3-methylhexyloxy)pentyl, 3-(2,4-dimethylpentyloxy)pentyl, 3-(1-ethyl-3-methylbutoxy)pentyl.

The scope of the present invention includes the (R)- and (S)-isomers and the racemates of compounds of the formula I having chiral centers.

With a view to the intended use of the triazolopyrimidines of the formula I, particular preference is given to the following meanings of the substituents, in each case on their own or in combination:

Preference is given to compounds I in which the group $R^1$ has at most 12 carbon atoms.

The alkyl groups in $R^1$ in formula I are preferably straight-chain or mono-, di-, tri- or polybranched, in particular a straight-chain alkyl group.

In addition, preference is given to compounds of the formula I which, in $R^1$, are branched at the α carbon atom. They are described by formula Ia:

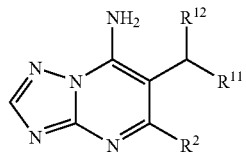

Ia in which $R^{11}$ is $C_3$-$C_{10}$-alkyl or $C_5$-$C_{10}$-alkoxyalkyl and $R^{12}$ is $C_1$-$C_4$-alkyl, in particular methyl, where $R^{11}$ and $R^{12}$ together have at most 12 carbon atoms and are unsubstituted or may be substituted like $R^1$ in formula I.

If $R^1$ is a cyano-substituted alkyl group, the cyano group is preferably located at the terminal carbon atom.

Preference is given to compounds I in which $R^1$ is a straight-chain or mono-, di-, tri- or polybranched $C_5$-$C_{12}$-alkyl group which does not carry any further substituents.

In one embodiment of the compounds I according to the invention, $R^1$ is $C_5$-$C_{12}$-alkyl or $C_1$-$C_{11}$-alkoxy-$C_1$-$C_{11}$-alkyl, the total number of carbon atoms preferably being from 5 to 12. Particular preference is given in this case to $C_2$-$C_8$-alkoxypropyl groups.

Particular preference is given to compounds I in which $R^1$ is n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl.

In addition, preference is given to compounds of the formula I in which $R^1$ is n-heptyl, 1-methylhexyl, n-octyl, 1-methylheptyl, n-nonyl, 1-methyloctyl, 3,5,5-trimethylhexyl, n-decyl, 1-methylnonyl, n-undecyl, 1-methyldecyl, n-dodecyl or 1-methylundecyl.

In one preferred embodiment of the compounds I according to the invention, $R^2$ is ethyl.

In a further preferred embodiment of the compounds I according to the invention, $R^2$ is isopropyl.

In a further embodiment of the compounds I according to the invention, $R^2$ is 1-methylpropyl.

In a further embodiment of the compounds I according to the invention, $R^2$ is cyclopropyl.

In particular with a view to their use, preference is given to the compounds I compiled in the tables below. Moreover, the groups mentioned for a substituent in the tables are per se, independently of the combination in which they are mentioned, a particularly preferred embodiment of the substituent in question.

Table 1
Compounds of the formula I in which $R^1$ for each compound corresponds to one row of Table A and $R^2$ is ethyl Table 2
Compounds of the formula I in which $R^1$ for each compound corresponds to one row of Table A and $R^2$ is isopropyl Table 3
Compounds of the formula I in which $R^1$ for each compound corresponds to one row of Table A and $R^2$ is 1-methylpropyl Table 4
Compounds of the formula I in which $R^1$ for each compound corresponds to one row of Table A and $R^2$ is ethenyl Table 5
Compounds of the formula I in which $R^1$ for each compound corresponds to one row of Table A and $R^2$ is allyl Table 6
Compounds of the formula I in which $R^1$ for each compound corresponds to one row of Table A and $R^2$ is cyclopropyl.

TABLE A

| No. | $R^1$ |
|---|---|
| A-1 | $CH_2CH_2CH_2CH_2CH_3$ |
| A-2 | $CH(CH_3)CH_2CH_2CH_3$ |
| A-3 | $CH_2CH(CH_3)CH_2CH_3$ |
| A-4 | $CH_2CH_2CH(CH_3)CH_3$ |
| A-5 | $CH_2CH_2CH(CH_3)_2$ |
| A-6 | $CH(CH_3)CH(CH_3)CH_3$ |
| A-7 | $CH(CH_3)CH(CH_3)_2$ |
| A-8 | $CH_2C(CH_3)_3$ |
| A-9 | $CH_2CH_2CH_2CH_2CH_2CH_3$ |
| A-10 | $CH(CH_3)CH_2CH_2CH_2CH_3$ |
| A-11 | $CH_2CH(CH_3)CH_2CH_2CH_3$ |
| A-12 | $CH_2CH_2CH(CH_3)CH_2CH_3$ |
| A-13 | $CH_2CH_2CH(CH_3)_2CH_2$ |
| A-14 | $CH_2CH_2CH_2CH(CH_3)_2$ |
| A-15 | $CH(CH_3)CH(CH_3)CH_2CH_3$ |
| A-16 | $CH(CH_3)CH_2CH(CH_3)_2$ |
| A-17 | $CH_2CH_2C(CH_3)_3$ |
| A-18 | $CH(CH_3)CH_2CH(CH_3)CH_3$ |
| A-19 | $CH_2CH_2CH_2CH_2CH_2CH_3$ |
| A-20 | $CH(CH_3)CH_2CH_2CH_2CH_2CH_3$ |
| A-21 | $CH_2CH(CH_3)CH_2CH_2CH_2CH_3$ |
| A-22 | $CH_2CH_2CH(CH_3)CH_2CH_2CH_3$ |
| A-23 | $CH_2CH_2CH_2CH(CH_3)CH_2CH_3$ |
| A-24 | $CH_2CH_2CH_2CH_2CH(CH_3)CH_3$ |
| A-25 | $CH_2CH_2CH_2CH_2CH(CH_3)_2$ |
| A-26 | $CH(CH_3)CH(CH_3)CH_2CH_2CH_3$ |
| A-27 | $CH_2CH(CH_3)CH(CH_3)CH_2CH_3$ |
| A-28 | $CH_2CH_2CH_2C(CH_3)_3$ |
| A-29 | $CH(CH_3)CH_2CH(CH_3)CH_2CH_3$ |
| A-30 | $CH_2CH(CH_3)CH(CH_3)CH_2CH_3$ |
| A-31 | $CH(CH_3)CH_2CH_2CH(CH_3)CH_3$ |
| A-32 | $CH_2CH_2CH_2CH_2CH_2CH_2CH_2CH_3$ |
| A-33 | $CH(CH_3)CH_2CH_2CH_2CH_2CH_2CH_3$ |
| A-34 | $CH(CH_3)CH_2CH_2CH_2CH_2CH_2CH_3$ |
| A-35 | $CH_2CH(CH_3)CH_2CH_2CH_2CH_2CH_3$ |
| A-36 | $CH_2CH_2CH(CH_3)CH_2CH_2CH_2CH_3$ |
| A-37 | $CH_2CH_2CH_2CH_2CH(CH_3)CH_2CH_3$ |
| A-38 | $CH_2CH_2CH_2CH_2CH_2CH(CH_3)_2$ |
| A-39 | $CH_2CH_2CH_2CH_2C(CH_3)_3$ |
| A-40 | $CH(CH_3)CH(CH_3)CH_2CH_2CH_2CH_3$ |
| A-41 | $CH_2CH(CH_3)CH(CH_3)CH_2CH_2CH_3$ |
| A-42 | $CH_2CH_2C(CH_3)_2CH_2CH_3$ |
| A-43 | $CH(CH_3)CH_2CH_2CH_3)CH_2CH_3$ |
| A-44 | $CH(CH_3)CH(CH_3)CH_2CH_2CH_3$ |
| A-45 | $CH(CH_3)CH_2CH_2CH(CH_3)CH_2CH_3$ |
| A-46 | $CH(CH_3)CH_2CH_2CH_2CH(CH_3)_2$ |
| A-47 | $CH_2CH_2CH(CH_3)CH_2C(CH_3)_3$ |
| A-48 | $CH_2CH_2CH_2CH_2CH_2CH_2CH_2CH_2CH_3$ |
| A-49 | $CH(CH_3)CH_2CH_2CH_2CH_2CH_2CH_2CH_3$ |
| A-50 | $CH_2CH(CH_3)CH_2CH_2CH_2CH_2CH_2CH_3$ |
| A-51 | $CH_2CH_2CH(CH_3)CH_2CH_2CH_2CH_2CH_3$ |
| A-52 | $CH_2CH_2CH_2CH(CH_3)CH_2CH_2CH_2CH_3$ |
| A-53 | $CH_2CH_2CH_2CH_2CH(CH_3)CH_2CH_2CH_3$ |
| A-54 | $CH_2CH_2CH_2CH_2CH_2CH_2C(CH_3)_3$ |
| A-55 | $CH(CH_3)CH(CH_3)CH_2CH_2CH_2CH_2CH_3$ |
| A-56 | $CH_2CH(CH_3)CH(CH_3)CH_2CH_2CH_2CH_3$ |
| A-57 | $CH_2CH_2CH_2C(CH_3)_2CH_2CH_2CH_3$ |
| A-58 | $CH(CH_3)CH_2CH(CH_3)CH_2CH_2CH_2CH_3$ |
| A-59 | $CH(CH_3)CH(CH_3)CH_2CH_2CH_2CH_3$ |
| A-60 | $CH(CH_3)CH_2CH_2CH(CH_3)CH_2CH_2CH_3$ |
| A-61 | $CH(CH_3)CH_2CH_2CH_2C(CH_3)_3$ |
| A-62 | $CH_2CH(CH_3)CH_2CH_2CH(CH_3)_3$ |
| A-63 | $CH(CH_3)CH_2CH_2CH_2CH_2CH(CH_3)_2$ |
| A-64 | $CH(CH_3)CH_2CH_2CH_2CH_2CH(CH_3)_2$ |
| A-65 | $CH_2CH_2CH_2CH_2CH_2CH_2CH_2CH_2CH_2CH_3$ |
| A-66 | $CH(CH_3)CH_2CH_2CH_2CH_2CH_2CH_2CH_2CH_3$ |
| A-67 | $CH(CH_3)CH_2CH_2CH_2CH_2CH_2CH_2CH_2CH_3$ |
| A-68 | $CH_2CH(CH_3)CH_2CH_2CH_2CH_2CH_2CH_2CH_3$ |
| A-69 | $CH_2CH_2CH(CH_3)CH_2CH_2CH_2CH_2CH_2$ |
| A-70 | $CH_2CH_2CH_2CH(CH_3)CH_2CH_2CH_2CH_3$ |
| A-71 | $CH_2CH_2CH_2CH_2CH_2CH_2C(CH_3)_3$ |
| A-72 | $CH(CH_3)CH(CH_3)CH_2CH_2CH_2CH_2CH_2CH_3$ |

TABLE A-continued

| No. | R¹ |
|---|---|
| A-73 | CH$_2$CH(CH$_3$)CH(CH$_3$)CH$_2$CH$_2$CH$_2$CH$_2$CH$_3$ |
| A-74 | CH$_2$CH$_2$CH$_2$C(CH$_3$)$_2$CH$_2$CH$_2$CH$_2$CH$_3$ |
| A-75 | CH(CH$_3$)CH$_2$CH(CH$_3$)CH$_2$CH$_2$CH$_2$CH$_2$CH$_3$ |
| A-76 | CH$_2$CH(CH$_3$)CH(CH$_3$)CH$_2$CH$_2$CH$_2$CH$_2$CH$_3$ |
| A-77 | CH(CH$_3$)CH$_2$CH$_2$CH(CH$_3$)CH$_2$CH$_2$CH$_2$CH$_3$ |
| A-78 | CH(CH$_3$)CH$_2$CH$_2$CH$_2$CH(CH$_3$)CH$_2$CH$_2$CH$_3$ |
| A-79 | CH(CH$_3$)CH$_2$CH$_2$CH$_2$CH$_2$CH(CH$_3$)CH$_2$CH$_3$ |
| A-80 | CH(CH$_3$)CH$_2$CH$_2$CH$_2$CH$_2$CH$_2$CH(CH$_3$)$_2$ |
| A-81 | CH(CH$_3$)CH$_2$CH$_2$CH$_2$CH$_2$CH$_2$C(CH$_3$)CH$_3$ |
| A-82 | CH$_2$CH(CH$_3$)CH$_2$CH$_2$CH$_2$CH$_2$CH(CH$_3$)CH$_3$ |
| A-83 | CH(CH$_3$)CH$_2$CH$_2$CH$_2$CH$_2$C(CH$_3$)$_3$ |
| A-84 | CH$_2$CH(CH$_3$)CH$_2$CH$_2$CH$_2$C(CH$_3$)$_3$ |
| A-85 | CH$_2$CH$_2$CH$_2$CH$_2$CH$_2$CH$_2$CH$_2$CH$_2$CH$_2$CH$_3$ |
| A-86 | CH(CH$_3$)CH$_2$CH$_2$CH$_2$CH$_2$CH$_2$CH$_2$CH$_2$CH$_2$CH$_3$ |
| A-87 | CH(CH$_3$)CH$_2$CH$_2$CH$_2$CH$_2$CH$_2$CH$_2$CH$_2$CH$_2$CH$_3$ |
| A-88 | CH$_2$CH$_2$CH(CH$_3$)CH$_2$CH$_2$CH$_2$CH$_2$CH$_2$CH$_3$ |
| A-89 | CH$_2$CH$_2$CH(CH$_3$)CH$_2$CH$_2$CH$_2$CH$_2$CH$_2$CH$_3$ |
| A-90 | CH$_2$CH$_2$CH$_2$CH$_2$CH(CH$_3$)CH$_2$CH$_2$CH$_2$CH$_3$ |
| A-91 | CH$_2$CH$_2$CH$_2$CH$_2$CH$_2$CH$_2$C(CH$_3$)$_3$ |
| A-92 | CH(CH$_3$)CH(CH$_3$)CH$_2$CH$_2$CH$_2$CH$_2$CH$_2$CH$_3$ |
| A-93 | CH(CH$_3$)CH(CH$_3$)CH$_2$CH$_2$CH$_2$CH$_2$CH$_2$CH$_3$ |
| A-94 | CH$_2$CH$_2$CH$_2$C(CH$_3$)$_2$CH$_2$CH$_2$CH$_2$CH$_2$CH$_3$ |
| A-95 | CH(CH$_3$)CH$_2$CH(CH$_3$)CH$_2$CH$_2$CH$_2$CH$_2$CH$_3$ |
| A-96 | CH$_2$CH(CH$_3$)CH(CH$_3$)CH$_2$CH$_2$CH$_2$CH$_2$CH$_3$ |
| A-97 | CH(CH$_3$)CH$_2$CH$_2$CH(CH$_3$)CH$_2$CH$_2$CH$_2$CH$_3$ |
| A-98 | CH(CH$_3$)CH$_2$CH$_2$CH$_2$CH(CH$_3$)CH$_2$CH$_2$CH$_3$ |
| A-99 | CH(CH$_3$)CH$_2$CH$_2$CH$_2$CH$_2$CH(CH$_3$)CH$_2$CH$_3$ |
| A-100 | CH(CH$_3$)CH$_2$CH$_2$CH$_2$CH$_2$CH$_2$CH(CH$_3$)CH$_2$CH$_3$ |
| A-101 | CH(CH$_3$)CH$_2$CH$_2$CH$_2$CH$_2$CH$_2$CH$_2$CH(CH$_3$)$_2$ |
| A-102 | CH$_2$CH(CH$_3$)CH$_2$CH$_2$CH$_2$CH(CH$_3$)CH$_2$CH$_3$ |
| A-103 | CH$_2$CH(CH$_3$)CH$_2$CH$_2$CH$_2$CH(CH$_3$)CH$_2$CH$_3$ |
| A-104 | CH$_2$CH$_2$CH(CH$_3$)CH$_2$CH$_2$CH$_2$CH(CH$_3$)$_2$ |
| A-105 | CH$_2$CH(CH$_3$)CH$_2$CH$_2$CH$_2$CH$_2$C(CH$_3$)$_3$ |
| A-106 | CH$_2$CH$_2$CH$_2$CH$_2$CH$_2$CH$_2$CH$_2$CH$_2$CH$_2$CH$_2$CH$_3$ |
| A-107 | CH(CH$_3$)CH$_2$CH$_2$CH$_2$CH$_2$CH$_2$CH$_2$CH$_2$CH$_2$CH$_2$CH$_3$ |
| A-108 | CH$_2$CH(CH$_3$)CH$_2$CH$_2$CH$_2$CH$_2$CH$_2$CH$_2$CH$_2$CH$_3$ |
| A-109 | CH$_2$CH$_2$CH(CH$_3$)CH$_2$CH$_2$CH$_2$CH$_2$CH$_2$CH$_2$CH$_3$ |
| A-110 | CH$_2$CH$_2$CH$_2$CH(CH$_3$)CH$_2$CH$_2$CH$_2$CH$_2$CH$_2$CH$_2$ |
| A-111 | CH$_2$CH$_2$CH$_2$CH$_2$CH(CH$_3$)CH$_2$CH$_2$CH$_2$CH$_2$CH$_3$ |
| A-112 | CH$_2$CH$_2$CH$_2$CH$_2$CH(CH$_3$)CH$_2$CH$_2$CH$_2$CH$_2$CH$_3$ |
| A-113 | CH$_2$CH$_2$CH$_2$CH$_2$CH$_2$CH(CH$_3$)CH$_2$CH$_2$CH$_2$CH$_3$ |
| A-114 | CH$_2$CH$_2$CH$_2$CH$_2$CH$_2$CH$_2$CH(CH$_3$)CH$_2$CH$_2$CH$_3$ |
| A-115 | CH$_2$CH$_2$CH$_2$CH$_2$CH$_2$CH$_2$CH$_2$CH(CH$_3$)CH$_2$CH$_3$ |
| A-116 | CH$_2$CH$_2$CH$_2$CH$_2$CH$_2$CH$_2$CH$_2$CH$_2$CH(CH$_3$)$_2$ |
| A-117 | CH(CH$_3$)CH(CH$_3$)CH$_2$CH$_2$CH$_2$CH$_2$CH$_2$CH$_2$CH$_3$ |
| A-118 | CH$_2$CH(CH$_3$)CH(CH$_3$)CH$_2$CH$_2$CH$_2$CH$_2$CH$_2$CH$_3$ |
| A-119 | CH$_2$CH$_2$CH$_2$C(CH$_3$)$_2$CH$_2$CH$_2$CH$_2$CH$_2$CH$_3$ |
| A-120 | CH$_2$CH$_2$CH$_2$CH$_2$CH(CH$_3$)CH$_2$CH$_2$CH$_2$CH$_2$CH$_3$ |
| A-121 | CH(CH$_3$)CH$_2$CH(CH$_3$)CH$_2$CH$_2$CH$_2$CH$_2$CH$_2$CH$_3$ |
| A-122 | CH(CH$_3$)CH$_2$CH$_2$CH(CH$_3$)CH$_2$CH$_2$CH$_2$CH$_2$CH$_3$ |
| A-123 | CH(CH$_3$)CH$_2$CH$_2$CH$_2$CH(CH$_3$)CH$_2$CH$_2$CH$_2$CH$_3$ |
| A-124 | CH(CH$_3$)CH$_2$CH$_2$CH$_2$CH$_2$CH(CH$_3$)CH$_2$CH$_2$CH$_3$ |
| A-125 | CH(CH$_3$)CH$_2$CH$_2$CH$_2$CH$_2$CH$_2$CH(CH$_3$)CH$_2$CH$_3$ |
| A-126 | CH(CH$_3$)CH$_2$CH$_2$CH$_2$CH$_2$CH$_2$CH$_2$CH(CH$_3$)CH$_2$CH$_3$ |
| A-127 | CH$_2$CH(CH$_3$)CH$_2$CH$_2$CH$_2$CH$_2$CH(CH$_3$)CH$_2$CH$_3$ |
| A-128 | CH$_2$CH$_2$CH(CH$_3$)CH$_2$CH$_2$CH$_2$CH$_2$CH(CH$_3$)CH$_2$CH$_3$ |
| A-129 | CH$_2$CH$_2$CH$_2$CH(CH$_3$)CH$_2$CH$_2$CH$_2$CH(CH$_3$)CH$_2$CH$_3$ |
| A-130 | CH$_2$CH(CH$_3$)CH$_2$CH$_2$CH$_2$CH$_2$C(CH$_3$)$_3$ |
| A-131 | CH$_2$CH$_2$CH$_2$—O—CH$_3$ |
| A-132 | CH$_2$CH$_2$CH$_2$—O—CH$_2$CH$_3$ |
| A-133 | CH$_2$CH$_2$CH$_2$—O—CH$_2$CH$_2$CH$_3$ |
| A-134 | CH$_2$CH$_2$CH$_2$—O—CH$_2$CH$_2$CH$_2$CH$_3$ |
| A-135 | CH$_2$CH$_2$CH$_2$—O—CH$_2$CH$_2$CH$_2$CH$_2$CH$_3$ |
| A-136 | CH$_2$CH$_2$CH$_2$—O—CH$_2$CH$_2$CH$_2$CH$_2$CH$_2$CH$_3$ |
| A-137 | CH$_2$CH$_2$CH$_2$—O—CH$_2$CH$_2$CH$_2$CH$_2$CH$_2$CH$_2$CH$_3$ |
| A-138 | CH$_2$CH$_2$CH$_2$—O—CH$_2$CH$_2$CH$_2$CH$_2$CH$_2$CH$_2$CH$_2$CH$_3$ |
| A-139 | CH$_2$CH$_2$CH$_2$—O—CH$_2$CH$_2$CH$_2$CH$_2$CH$_2$CH$_2$CH$_2$CH$_2$CH$_3$ |
| A-140 | CH$_2$CH$_2$CH$_2$—O—CH(CH$_3$)$_2$ |
| A-141 | CH$_2$CH$_2$CH$_2$—O—C(CH$_3$)$_3$ |
| A-142 | CH$_2$CH$_2$CH$_2$—O—CH$_2$C(CH$_3$)$_3$ |
| A-143 | CH$_2$CH$_2$CH$_2$—O—CH(CH$_3$)CH$_2$C(CH$_3$)$_3$ |
| A-144 | CH$_2$CH$_2$CH$_2$—O—CH(CH$_2$CH$_3$)CH$_2$C(CH$_3$)$_3$ |
| A-145 | CH$_2$CH$_2$CH$_2$—O—CH$_2$CH(CH$_3$)CH$_2$CH(CH$_3$)$_2$ |
| A-146 | CH$_2$CH$_2$CH$_2$—O—CH$_2$CH(CH$_2$CH$_3$)CH$_2$CH$_2$CH$_3$ |
| A-147 | CH$_2$CH$_2$CH$_2$—O—CH$_2$CH$_2$CH(CH$_3$)CH$_2$CH(CH$_3$)$_2$ |
| A-148 | CH$_2$CH$_2$CH$_2$—O—CH$_2$CH$_2$CH(CH$_3$)CH$_2$C(CH$_3$)$_3$ |
| A-149 | CH$_2$CH$_2$CH$_2$—O—CH$_2$CH$_2$CH(CH$_3$)CH$_2$CH$_2$CH(CH$_3$)$_2$ |
| A-150 | CH$_2$CH$_2$CH$_2$—O—CH$_2$CH$_2$CH(CH$_3$)CH$_2$CH$_2$CH$_2$CH(CH$_3$)$_2$ |
| A-151 | CH$_2$CH$_2$CH$_2$CH$_2$—O—CH$_3$ |
| A-152 | CH$_2$CH$_2$CH$_2$CH$_2$—O—CH$_2$CH$_3$ |
| A-153 | CH$_2$CH$_2$CH$_2$CH$_2$—O—CH$_2$CH$_2$CH$_3$ |
| A-154 | CH$_2$CH$_2$CH$_2$CH$_2$—O—CH$_2$CH$_2$CH$_2$CH$_3$ |
| A-155 | CH$_2$CH$_2$CH$_2$CH$_2$—O—CH$_2$CH$_2$CH$_2$CH$_2$CH$_3$ |
| A-156 | CH$_2$CH$_2$CH$_2$CH$_2$—O—CH$_2$CH$_2$CH$_2$CH$_2$CH$_2$CH$_3$ |
| A-157 | CH$_2$CH$_2$CH$_2$CH$_2$—O—CH$_2$CH$_2$CH$_2$CH$_2$CH$_2$CH$_2$CH$_3$ |
| A-158 | CH$_2$CH$_2$CH$_2$CH$_2$—O—CH$_2$CH$_2$CH$_2$CH$_2$CH$_2$CH$_2$CH$_2$CH$_3$ |
| A-159 | CH$_2$CH$_2$CH$_2$CH$_2$—O—CH(CH$_3$)$_2$ |
| A-160 | CH$_2$CH$_2$CH$_2$CH$_2$—O—C(CH$_3$)$_3$ |
| A-161 | CH$_2$CH$_2$CH$_2$CH$_2$—O—CH$_2$C(CH$_3$)$_3$ |
| A-162 | CH$_2$CH$_2$CH$_2$CH$_2$—O—CH(CH$_3$)CH$_2$C(CH$_3$)$_3$ |
| A-163 | CH$_2$CH$_2$CH$_2$CH$_2$—O—CH(CH$_2$CH$_3$)CH$_2$C(CH$_3$)$_3$ |

TABLE A-continued

| No. | R$^1$ |
|---|---|
| A-164 | CH$_2$CH$_2$CH$_2$CH$_2$—O—CH$_2$CH(CH$_3$)CH$_2$CH(CH$_3$)$_2$ |
| A-165 | CH$_2$CH$_2$CH$_2$CH$_2$—O—CH$_2$CH(CH$_2$CH$_3$)CH$_2$CH$_2$CH$_3$ |
| A-166 | CH$_2$CH$_2$CH$_2$CH$_2$—O—CH$_2$CH$_2$CH(CH$_3$)CH$_2$CH(CH$_3$)$_2$ |
| A-167 | CH$_2$CH$_2$CH$_2$CH$_2$—O—CH$_2$CH$_2$CH(CH$_3$)CH$_2$C(CH$_3$)$_3$ |
| A-168 | CH$_2$CH$_2$CH$_2$CH$_2$—O—CH$_2$CH$_2$CH(CH$_3$)CH$_2$CH$_2$CH(CH$_3$)$_2$ |
| A-169 | CH$_2$CH$_2$CH$_2$CH$_2$—O—CH$_2$CH$_2$CH(CH$_3$)CH$_2$CH$_2$CH$_2$CH(CH$_3$)$_2$ |
| A-170 | CH$_2$CH$_2$CH$_2$CH$_2$CH$_2$—O—CH$_3$ |
| A-171 | CH$_2$CH$_2$CH$_2$CH$_2$CH$_2$—O—CH$_2$CH$_3$ |
| A-172 | CH$_2$CH$_2$CH$_2$CH$_2$CH$_2$—O—CH$_2$CH$_2$CH$_3$ |
| A-173 | CH$_2$CH$_2$CH$_2$CH$_2$CH$_2$—O—CH$_2$CH$_2$CH$_2$CH$_3$ |
| A-174 | CH$_2$CH$_2$CH$_2$CH$_2$CH$_2$—O—CH$_2$CH$_2$CH$_2$CH$_2$CH$_3$ |
| A-175 | CH$_2$CH$_2$CH$_2$CH$_2$CH$_2$—O—CH$_2$CH$_2$CH$_2$CH$_2$CH$_2$CH$_3$ |
| A-176 | CH$_2$CH$_2$CH$_2$CH$_2$CH$_2$—O—CH$_2$CH$_2$CH$_2$CH$_2$CH$_2$CH$_2$CH$_3$ |
| A-177 | CH$_2$CH$_2$CH$_2$CH$_2$CH$_2$—O—CH$_2$CH$_2$CH$_2$CH$_2$CH$_2$CH$_2$CH$_2$CH$_3$ |
| A-178 | CH$_2$CH$_2$CH$_2$CH$_2$CH$_2$—O—CH(CH$_3$)$_2$ |
| A-179 | CH$_2$CH$_2$CH$_2$CH$_2$CH$_2$—O—C(CH$_3$)$_3$ |
| A-180 | CH$_2$CH$_2$CH$_2$CH$_2$CH$_2$—O—CH$_2$C(CH$_3$)$_3$ |
| A-181 | CH$_2$CH$_2$CH$_2$CH$_2$CH$_2$—O—CH(CH$_3$)CH$_2$C(CH$_3$)$_3$ |
| A-182 | CH$_2$CH$_2$CH$_2$CH$_2$CH$_2$—O—CH(CH$_2$CH$_3$)CH$_2$C(CH$_3$)$_3$ |
| A-183 | CH$_2$CH$_2$CH$_2$CH$_2$CH$_2$—O—CH$_2$CH(CH$_3$)CH$_2$CH(CH$_3$)$_2$ |
| A-184 | CH$_2$CH$_2$CH$_2$CH$_2$CH$_2$—O—CH$_2$CH(CH$_2$CH$_3$)CH$_2$CH$_2$CH$_3$ |
| A-185 | CH$_2$CH$_2$CH$_2$CH$_2$CH$_2$—O—CH$_2$CH$_2$CH(CH$_3$)CH$_2$CH$_2$CH(CH$_3$)$_2$ |
| A-186 | CH$_2$CH$_2$CH$_2$CH$_2$CH$_2$—O—CH$_2$CH$_2$CH(CH$_3$)CH$_2$CH(CH$_3$)$_2$ |
| A-187 | CH$_2$CH$_2$CH$_2$CH$_2$CH$_2$—O—CH$_2$CH$_2$CH(CH$_3$)CH$_2$C(CH$_3$)$_3$ |

The compounds I are suitable as fungicides. They are distinguished by an outstanding effectiveness against a broad spectrum of phytopathogenic fungi, especially from the classes of the Ascomycetes, Deuteromycetes, Oomycetes and Basidiomycetes, especially from the class of the Oomycetes. Some are systemically effective and they can be used in plant protection as foliar, fungicide, as fungicide for seed dressing and soil fungicides.

They are particularly important in the control of a multitude of fungi on various cultivated plants, such as wheat, rye, barley, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:
  *Alternaria* species on fruit and vegetables,
  *Bipolaris* and *Drechslera* species on cereals, rice and lawns,
  *Blumeria graminis* (powdery mildew) on cereals,
  *Botrytis cinerea* (gray mold) on strawberries, vegetables, ornamental plants and grapevines,
  *Bremia lactucae* on salad,
  *Erysiphe cichoracearum* and *Sphaerotheca fuliginea* on cucurbits,
  *Fusarium* and *Verticillium* species on various plants,
  *Mycosphaerella* species on cereals, bananas and peanuts,
  *Peronospora* species on cabbage and onions,
  *Phakopsora pachyrhizi* and *P. meibomiae* on soybeans,
  *Phytophthora infestans* on potatoes and tomatoes,
  *Phytophthora capsici* on peppers,
  *Plasmopara viticola* on grapevines,
  *Podosphaera leucotricha* on apples,
  *Pseudocercosporella herpotrichoides* on wheat and barley,
  *Pseudoperonospora* species on hops and cucumbers,
  *Puccinia* species on cereals,
  *Pyricularia oryzae* on rice,
  *Pythium aphanidermatum* on lawns,
  *Rhizoctonia* species on cotton, rice and lawns,
  *Septoria tritici* and *Stagonospora nodorum* on wheat,
  *Uncinula necator* on grapevines,
  *Ustilago* species on cereals and sugar cane, and
  *Venturia* species (scab) on apples and pears.

They are particularly suitable for controlling harmful fungi from the class of the Oomycetes, such as *Peronospora* species, *Phytophthora* species, *Plasmopara viticola* and *Pseudoperonospora* species.

The compounds I are also suitable for controlling harmful fungi, such as *Paecilomyces variotii*, in the protection of materials (e.g. wood, paper, paint dispersions, fibers or fabrics) and in the protection of stored products.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise between 0.1 and 95%, preferably between 0.5 and 90%, by weight of active compound.

When employed in plant protection, the amounts applied are, depending on the kind of effect desired, between 0.01 and 2.0 kg of active compound per ha.

In seed treatment, amounts of active compound of 1 to 1000 g/100 kg, preferably 5 to 100 g/100 kg of seed are generally required.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted into the customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable are essentially:
  water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutyinaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The following are examples of formulations: 1. Products for dilution with water
A Water-Soluble Concentrates (SL)

10 parts by weight of a compound according to the invention are dissolved in water or in a water-soluble solvent. As an alternative, wetters or other auxiliaries are added. The active compound dissolves upon dilution with water.

B Dispersible Concentrates (DC)

20 parts by weight of a compound according to the invention are dissolved in cyclohexanone with addition of a dispersant, for example polyvinylpyrrolidone. Dilution with water gives a dispersion.

C Emulsifiable Concentrates (EC)

15 parts by weight of a compound according to the invention are dissolved in xylene with addition of calcium dodecylbenzenesulfonate and castor oil ethoxylate (in each case 5%). Dilution with water gives an emulsion.

D Emulsions (EW, EO)

40 parts by weight of a compound according to the invention are dissolved in xylene with addition of calcium dodecylbenzenesulfonate and castor oil ethoxylate (in each case 5%). This mixture is introduced into water by means of an emulsifying machine (Ultraturrax) and made into a homogeneous emulsion. Dilution with water gives an emulsion.

E Suspensions (SC, OD)

In an agitated ball mill, 20 parts by weight of a compound according to the invention are comminuted with addition of dispersants, wetters and water or an organic solvent to give a fine active compound suspension. Dilution with water gives a stable suspension of the active compound.

F Water-Dispersible Granules and Water-Soluble Granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active compound.

G Water-Dispersible Powders and Water-Soluble Powders (WP, SP)

75 parts by weight of a compound according to the invention are ground in a rotor-stator mill with addition of dispersants, wetters and silica gel. Dilution with water gives a stable dispersion or solution of the active compound.

2. Products to be Applied Undiluted
H Dustable Powders (DP)

5 parts by weight of a compound according to the invention are ground finely and mixed intimately with 95% of finely divided kaolin. This gives a dustable product.

I Granules (GR, FG, GG, MG)

0.5 part by weight of a compound according to the invention is ground finely and associated with 95.5% carriers. Current methods are extrusion, spray-drying or the fluidized bed. This gives granules to be applied undiluted.

J ULV Solutions (UL)

10 parts by weight of a compound according to the invention are dissolved in an organic solvent, for example xylene. This gives a product to be applied undiluted.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), by which it is possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate not until immediately prior to use (tank mix). These agents can be admixed with the agents according to the invention in a weight ratio of 1:10 to 10:1.

The compositions according to the invention can, in the use form as fungicides, also be present together with other active compounds, e.g. with herbicides, insecticides, growth regulators, fungicides or else with fertilizers. Mixing the compounds I or the compositions comprising them in the application form as fungicides with other fungicides results in many cases in an expansion of the fungicidal spectrum of activity being obtained.

The following list of fungicides, in conjunction with which the compounds according to the invention can be used, is intended to illustrate the possible combinations but not limit them:
- acylalanines, such as benalaxyl, metalaxyl, ofurace or oxadixyl,
- amine derivatives, such as aldimorph, dodine, dodemorph, fenpropimorph, fenpropidin, guazatine, iminoctadine, spiroxamine or tridemorph,
- anilinopyrimidines, such as pyrimethanil, mepanipyrim or cyprodinyl,
- antibiotics, such as cycloheximide, griseofulvin, kasugamycin, natamycin, polyoxin or streptomycin,
- azoles, such as bitertanol, bromoconazole, cyproconazole, difenoconazole, dinitroconazole, enilconazole, epoxiconazole, fenbuconazole, fluquinconazole, flusilazole, hexaconazole, imazalil, metconazole, myclobutanil, penconazole, propiconazole, prochloraz, prothioconazole, tebuconazole, triadimefon, triadimenol, triflumizole or triticonazole,
- dicarboximides, such as iprodione, myclozolin, procymidone or vinclozolin,
- dithiocarbamates, such as ferbam, nabam, maneb, mancozeb, metam, metiram, propineb, polycarbamate, thiram, ziram or zineb,
- heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine,
- copper fungicides, such as Bordeaux mixture, copper acetate, copper oxychloride or basic copper sulfate,
- nitrophenyl derivatives, such as binapacryl, dinocap, dinobuton or nitrophthal-isopropyl,
- phenylpyrroles, such as fenpiclonil or fludioxonil,
- sulfur,
- other fungicides, such as acibenzolar-S-methyl, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, phosphorous acid, fosetyl, fosetyl-aluminum, iprovalicarb, hexachlorobenzene, metrafenone, pencycuron, propamocarb, phthalide, toiclofosmethyl, quintozene or zoxamide,
- strobilurins, such as azoxystrobin, dimoxystrobin, enestroburin, fluoxastrobin, kresoxim-methyl, metominostrobin, orysastrobin, picoxystrobin, pyraclostrobin or trifloxystrobin,
- sulfenic acid derivatives, such as captafol, captan, dichlofluanid, folpet or tolylfluanid,
- cinnamides and analogous compounds, such as dimethomorph, flumetover or flumorph.

SYNTHESIS EXAMPLES

The procedures described in the following synthesis examples were used to prepare further compounds I by appropriate modification of the starting materials. The compounds thus obtained are listed in the table below, together with physical data.

Example 1

Preparation of 4-cyanoundecan-3-one

At −70° C., a solution of 0.495 mol of butyllithium in hexane was added to a solution of 0.45 mol of decanitrile in 300 ml of tetrahydrofuran (THF), the mixture was stirred at this temperature for about 3 hours and 0.45 mol of ethyl propionate was then added. The mixture was subsequently stirred at 20-25° C. for about 16 hours, 200 ml of water were then added and the mixture was acidified with dil. HCl solution. After the phases had separated, the organic phase was removed, washed with water, dried and freed from the solvent. 91 g of the title compound remained.

Example 2

Preparation of 7-amino-5-ethyl-6-octyl[1,2,4]triazolo[1,5-a]pyrimidine

A mixture of in each case 1.27 mol of 5-cyanoundecan-3-one from Example 1 and 3-amino-1,2,4-triazole and 0.25 mol of p-toluenesulfonic acid in 900 ml of mesitylene was heated at 170° C. for about 4 hours. After cooling to about 20-25° C., the precipitate was filtered off and then taken up in dichloromethane. After washing with water and drying, the solvent was distilled off from the solution, giving, as residue, 124 g of the title compound of m.p. 196° C.

TABLE I

Compounds of the formula I

| No. | $R^1$ | $R^2$ | Phys. data (m.p. [° C.]) |
|---|---|---|---|
| I-1 | $CH(CH_3)(CH_2)_5CH_3$ | $CH_2CH_3$ | 137 |
| I-2 | $(CH_2)_7CH_3$ | $CH_2CH_3$ | 196 |
| I-3 | $(CH_2)_2CH(CH_3)CH_2C(CH_3)_3$ | $CH_2CH_3$ | 197-198 |
| I-4 | $(CH_2)_7CH_3$ | $CH(CH_3)_2$ | 178 |
| I-5 | $(CH_2)_7CH_3$ | Cyclopropyl | 223 |
| I-6 | $(CH_2)_4CH_3$ | $CH_2CH_3$ | 179-180 |
| I-7 | $(CH_2)_5CH_3$ | $CH_2CH_3$ | 218-219 |
| I-8 | $(CH_2)_6CH_3$ | $CH_2CH_3$ | 198-199 |
| I-9 | $(CH_2)_8CH_3$ | $CH_2CH_3$ | 189-190 |
| I-10 | $(CH_2)_9CH_3$ | $CH_2CH_3$ | 180-181 |
| I-11 | $(CH_2)_{10}CH_3$ | $CH_2CH_3$ | 206-207 |
| I-12 | $(CH_2)_5CH_3$ | $CH(CH_3)_2$ | 214-215 |
| I-13 | $(CH_2)_6CH_3$ | $CH(CH_3)_2$ | 185-186 |
| I-14 | $(CH_2)_9CH_3$ | $CH(CH_3)_2$ | 145-146 |

TABLE I-continued

Compounds of the formula I

| No. | $R^1$ | $R^2$ | Phys. data (m.p. [° C.]) |
|---|---|---|---|
| I-15 | $(CH_2)_3O(CH_2)_4CH_3$ | $CH_2CH_3$ | 144-146 |
| I-16 | $(CH_2)_5CN$ | $CH_2CH_3$ | 158-160 |

Examples of the action against harmful fungi

The fungicidal action of the compounds of the formula I was demonstrated by the following experiments:

The active compounds were prepared as a stock solution comprising 25 mg of active compound which was made up to 10 ml using a mixture of acetone and/or DMSO and the emulsifier Uniperol® EL (wetting agent having emulsifying and dispersing agent based on ethoxylated alkylphenols) in a ratio by volume of solvent/emulsifier of 99/1. The mixture was then made up to 100 ml with water. This stock solution was, using the solvent/emulsifier/water mixture described, diluted to the active compound concentration stated below.

Use Example 1

Activity Against *Peronospora* of Grapevines Caused by *Plasmopara viticola*

Leaves of potted vines were sprayed to runoff point with an aqueous suspension having the concentration of active compound stated below. The next day, the undersides of the leaves were inoculated with an aqueous sporangia suspension of *Plasmopara viticola*. The vines were then initially placed in a water-vapor-saturated chamber at 24° C. for 48 hours and then in a greenhouse at temperatures between 20° C. and 30° C. for 5 days. After this time, the plants were once more placed in a humid chamber for 16 hours to promote the eruption of sporangiophores. The extent of the development of the infection on the undersides of the leaves was then determined visually.

In this test, the plants which had been treated with 250 ppm of the compounds 1-1 or 1-2 showed no infection, whereas the untreated plants were 95% infected.

Use Example 2

Activity Against Late Blight of Tomatoes Caused by *Phytophthora infestans*, Protective Treatment Leaves of potted tomato plants were sprayed to runoff point with an aqueous suspension having the concentration of active compounds stated below. The next day, the leaves were infected with an aqueous sporangia suspension of *Phytophthora infestans*. The plants were then placed in a water-vapor-saturated chamber at temperatures between 18° C. and 20° C. After 6 days, the late blight on the untreated, but infected control plants had developed to such an extent that the infection could be determined visually in %.

In this test, the plants which had been treated with 250 ppm of the compounds I-1, I-2, I-8, I-9, I-10 or I-11 showed no infection, whereas the untreated plants were 100% infected.

Use Example 3

Activity Against *Peronospora* of Grapevines Caused by *Plasmopara viticola*, Protective Application Leaves of potted vines of the cultivar "Müller-Thurgau" were sprayed to runoff point with an aqueous suspension having the concentration of active compounds stated below. To be able to assess the persistency of the substances, the plants were, after the spray coating had dried on, placed in a greenhouse for 7 days. Only then were the leaves inoculated with an aqueous zoospore suspension of *Plasmopara viticola*. The vines were then initially placed in a water-vapor-saturated chamber at 24° C. for 48 hours and then in the greenhouse at temperatures between 20° C. and 30° C. for 5 or 7 days. After this time, the plants were once more placed in a humid chamber for 16 hours to promote the eruption of sporangiophores. The extent of the development of the infection on the undersides of the leaves was then determined visually.

In the test arrangement where there is a 5 day protective application, the plants which had been treated with 250 ppm of the compound 1-4 showed an infection of 5%, whereas the untreated plants were 75% infected. In the test arrangement where there is a 7 day protective application, the plants which had been treated with 250 ppm of the compounds I-8, I-9, I-10, I-11, I-12 or I-13 showed an infection of at most 7%, whereas the untreated plants were 80% infected.

We claim:

1. A triazolopyrimidine of the formula I

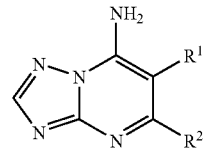

in which the substituents are as defined below:
$R^1$ is $C_5$-$C_{12}$-alkyl
$R^2$ is ethyl or $CH_2CH=CH_2$.

2. The compound of the formula I according to claim 1, in which $R^2$ is ethyl.

3. The compound of the formula I according to claim 1, in which $R^1$ is an unsubstituted straight-chain or mono-, di- or tribranched alkyl chain having up to 12 carbon atoms.

4. Triazolopyrimidines of the formula I according to claim 1 selected from the group consisting of:
   5-ethyl-6-(1-methylheptyl)-[1,2,4]triazolo[1,5-a]pyrimidin-7-ylamine;
   5-ethyl-6-octyl-[1,2,4]triazolo[1,5-a]pyrimidin-7-ylamine;
   5-ethyl-6-(3,5,5-trimethylhexyl)-[1,2,4]triazolo[1,5-a]pyrimidin-7-ylamine;
   5-ethyl-6-pentyl-[1,2,4]triazolo[1,5-a]pyrimidin-7-ylamine;
   5-ethyl-6-hexyl-[1,2,4]triazolo[1,5-a]pyrimidin-7-ylamine;
   5-ethyl-6-heptyl-[1,2,4]triazolo[1,5-a]pyrimidin-7-ylamine;
   5-ethyl-6-nonyl-[1,2,4]triazolo[1,5-a]pyrimidin-7-ylamine;
   5-ethyl-6-undecyl-[1,2,4]triazolo [1,5-a]pyrimidin-7-ylamine.

5. A process for preparing compounds of the formula I according to any of claims 1 to 4 wherein β-keto esters of the formula II,

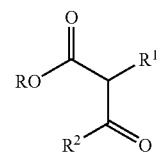

in which R is $C_1$-$C_4$-alkyl are reacted with 3-amino-1,2,4-triazole of the formula III

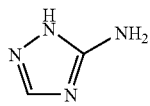

III to give 7-hydroxytriazolopyrimidines of the formula IV

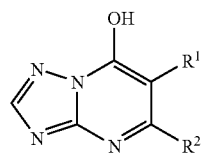

IV which are halogenated to give compounds of the formula V

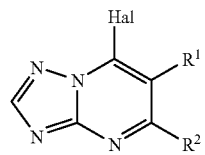

V in which Hal is chlorine or bromine and V is reacted with ammonia.

6. A compound of the formula IV or V according to claim 5.

7. A process for preparing compounds of the formula I according to any of claims 1 to 4 wherein acyl cyanides of the formula VI,

VI are reacted with 3-amino-1,2,4-triazole of the formula III.

8. A fungicidal composition comprising a solid or liquid carrier and a compound of the formula I according to any of claims 1 to 4.

9. Seed comprising a compound of the formula I according to any of claims 1 to 4 in an amount of 1 to 1000 g per 100 kg.

10. A method for controlling phytopathogenic harmful fungi, wherein the fungi or the materials, plants, the soil or seed to be protected against fungal attack are treated with an effective amount of the compound of the formula I according to any of claims 1 to 4.

* * * * *